United States Patent [19]

Steinbeck et al.

[11] 4,342,701
[45] Aug. 3, 1982

[54] PROCESS FOR THE PREPARATION OF 4,5-DINITRO-1,8-DIHYDROXYANTHRAQUINONE

[75] Inventors: Werner Steinbeck; Günter Gehrke, both of Cologne, Fed. Rep. of Germany

[73] Assignee: Bayer Aktiengesellschaft, Leverkusen, Fed. Rep. of Germany

[21] Appl. No.: 123,870

[22] Filed: Feb. 22, 1980

[30] Foreign Application Priority Data

Mar. 10, 1979 [DE] Fed. Rep. of Germany ....... 2909481

[51] Int. Cl.³ .............................................. C07C 49/74
[52] U.S. Cl. ..................................................... 260/383
[58] Field of Search .......................................... 260/383

[56] References Cited

U.S. PATENT DOCUMENTS

| | | | |
|---|---|---|---|
| 3,082,218 | 3/1963 | Buxbaum et al. | 260/383 |
| 3,636,008 | 1/1972 | Yamada et al. | 260/383 |
| 3,884,943 | 5/1975 | Wimkle | 260/383 |
| 4,158,009 | 6/1979 | Takeda et al. | 260/369 |

FOREIGN PATENT DOCUMENTS 1929808 12/1969 Fed. Rep. of Germany ...... 260/383

Primary Examiner—Thomas A. Waltz
Assistant Examiner—Raymond K. Covington
Attorney, Agent, or Firm—Sprung, Horn, Kramer & Woods

[57] ABSTRACT

95–99% pure 4,5-dinitro-1,8-dihydroxyanthraquinone which is essentially free from by-products is obtained by "direct nitration" of 1,8-dihydroxyanthraquinones or 1,8-dimethoxyanthraquinones if the concentrations of acid are chosen such that, when the nitration reaction and, if appropriate, the saponification reaction have ended, an 80–100% strength sulphuric acid is present, or such a sulphuric acid concentration is established by adding water, and the 4,5-dinitro-1,8-dihydroxyanthraquinone which crystallizes out is separated off.

3 Claims, No Drawings

PROCESS FOR THE PREPARATION OF 4,5-DINITRO-1,8-DIHYDROXYANTHRAQUINONE

The invention relates to an improved process for the preparation of technically pure 4,5-dinitro-1,8-dihydroxyanthraquinone. This important intermediate dyestuff product has hitherto been prepared in a technically pure form by a procedure in which anthraquinone-1,8-disulphonic acid is converted into 1,8-dichloroanthraquinone with sodium chlorate and this product is reacted with sodium phenolate to give 1,8-diphenoxyanthraquinone, which is then nitrated, and finally the nitration product is saponified.

However, because of the large number of stages of this process and because of the necessity of removing the dinitrophenol unavoidably obtained during hydrolysis of the nitration product, this process is relatively expensive. The preparation of 4,5-dinitro-1,8-dihydroxyanthraquinone is less expensive and thus significantly more profitable when anthraquinone-1,8-disulphonic acid is converted into 1,8-dihydroxyanthraquinone with calcium hydroxide and this product is nitrated with nitric acid in the presence of boric acid, or the disulphonic acid mentioned is converted into 1,8-dimethoxyanthraquinone by means of methanolic potassium hydroxide solution, this product is then nitrated in sulphuric acid and the methoxy groups are saponified (compare, for example, Endeavour XXXVIII, page 137, September 1976).

Both variants of this "direct nitration", however, have the disadvantage that relatively large amounts of 2,5-dinitro derivative and trinitro compounds are formed as undesired by-products.

It has now been found that a 4,5-dinitro-1,8-dihydroxyanthraquinone which is in general 95-99% pure and is essentially free from by-products is obtained by "direct nitration" of 1,8-dihydroxyanthraquinone or 1,8-dimethoxyanthraquinone if the acid concentration is chosen such that, when the nitration reaction and, if appropriate, the saponification reaction have ended, an 80-100% strength sulphuric acid is present, or such a sulphuric acid concentration is established by adding water, and 4,5-dinitro-1,8-dihydroxyanthraquinone which crystallises out is separated off.

The desired reaction product is separated off in the customary manner by filtration and subsequent washing with sulphuric acid and water. In the process according to the invention, virtually all of the undesired by-products remains in solution and, if desired, can be isolated from the mother liquor by precipitation with water.

In general, in carrying out the claimed process in practice, a procedure is followed in which 1 part of 1,8-dihydroxyanthraquinone is dissolved in a solution of 0.25-0.75 part of boric acid in 4-20 parts of concentrated sulphuric acid or oleum and is nitrated with 0.50-0.55 part of nitric acid or the appropriate amount of mixed acid at $-10°$ C. to 30° C. in a manner which is in itself known. The total amount of nitric acid is thereby consumed. Thereafter, the required sulphuric acid concentration of 80-100%, preferably 85-90%, is established by carefully adding water. During this addition, it is advantageous not to remove the heat of dilution immediately by external cooling, in order to enable the desired product to crystallise out slowly. In the other variant of the process according to the invention, 1 part of 1,8-dimethoxyanthraquinone is nitrated, in 4-20 parts of 90-100% strength sulphuric acid, with 0.45-0.50 part of nitric acid or the appropriate amount of mixed acid at $-10°$ C. to 30° C., without the addition of boric acid. The methoxy groups are then saponified by heating the mixture to 90°-120° C. for several hours.

In both variants, the reaction mixture is allowed to cool slowly to room temperature before the 4,5-dinitro-1,8-dihydroxyanthraquinone is filtered off with good suction and washed with sulphuric acid and then with water.

As already mentioned, 4,5-dinitro-1,8-dihydroxyanthraquinone is an important intermediate product for the preparation of valuable dyestuffs. For example, clear blue dyestuffs for polyesters are obtained from this compound by reduction of the nitro groups and optional subsequent halogenation (compare, for example, U.S. Pat. No. 2,990,413). Valuable dyestuffs for polyesters are also obtained by replacement of one nitro group by arylamine radicals and optional subsequent reduction of the nitro group which remains (compare U.S. Pat. No. 2,053,274).

The reaction of 4,5-dinitro-1,8-dihydroxyanthraquinone with optionally substituted aniline in the presence of boric acid gives 1,4-dianilino-5-nitro-8-hydroxyanthraquinones, which are green dyestuffs for polyesters (compare, for example, U.S. Pat. No. 3,444,215).

Reduction of one nitro group in 4,5-dinitro-1,8-dihydroxyanthraquinone and subsequent reaction of the product with alkyl- or aryl-amines in the presence of boric acid gives 1-alkyl(aryl)amino-4-amino-5-nitro-8-hydroxyanthraquinones, which are turquoise blue dyestuffs for polyesters (compare U.S. Pat. No. 3,883,567).

The 4,5-dinitro-1,8-dihydroxyanthraquinone obtainable by the process according to the invention is of high quality and can be employed directly for such dyestuff syntheses, without further purification operations.

In contrast, the "direct nitration products" obtained according to the state of the art are dyestuffs of inferior quality and with dull colour shades.

The "parts" mentioned above and in the examples below are parts by weight.

EXAMPLE 1

64 parts of 90% pure 1,8-dihydroxy-anthraquinone are dissolved in a solution of 32 parts of boric acid in 760 parts of 20% strength oleum at a maximum temperature of 50° C. 103 parts of mixed acid (33% of $HNO_3$, 67% of $H_2SO_4$) are then added dropwise in the course of 3 hours, whilst cooling at 0°-5° C., and stirring is continued at this temperature for a further 1 hour. 133 parts of water are now added dropwise in the course of 1.5 hours, during which the temperature may rise to 100° C. The mixture is stirred at 100° C. for 1 hour and cooled to 20°-25° C. and the crystalline precipitate is filtered off. It is washed with 145 parts of 88% strength sulphuric acid and then with water and, after drying, 59.9 parts of 99.2% pure 4,5-dinitro-1,8-dihydroxyanthraquinone, which contains 0.5% of the 2,5-dinitro compound and 0.2% of the 2,4,5-trinitro derivative, are obtained.

22 parts of a solid can be isolated from the mother liquor and the sulphuric acid washings by discharging this mixture onto ice-water, filtering, washing the material on the filter with water until neutral and drying it. The following nitration products were determined in this solid by quantitative column chromatography: 21.2% of 4,5-dinitro- DHA, 43.7% of 2,5-dinitro- DHA, 2.7% of 2,7-dinitro- +2,4,7-trinitro- DHA, 5.7% of 2,4,5-trinitro- DHA and 1.4% of 4-nitro- DHA. (1,8-Dihydroxy-anthraquinone=DHA)

EXAMPLE 2

The procedure followed is as indicated in Example 1. However, after the nitration, 155 parts of water are added dropwise instead of 133 parts. 66 parts of 96.9% pure 4,5-dinitro-1,8-dihydroxy-anthraquinone, which contains 0.9% of the 2,5-dinitro isomer and a trace of the trinitro derivative, are obtained.

17 parts of a solid of the following composition are obtained from the mother liquor and the sulphuric acid washings: 7.5% of 4,5-dinitro- DHA, 53.9% of 2,5-dinitro- DHA, 2.7% of 2,7-dinitro- +2,4,7-trinitro- DHA and 1.6% of 4-nitro- DHA.

EXAMPLE 3

The procedure is the same as in Example 1, but the nitration is carried out in 320 parts of 20% strength oleum instead of in 760 parts and the mixture is then diluted with only 38 parts of water. Yield: 54 parts of 95.1% pure 4,5-dinitro-1,8-dihydroxy-anthraquinone containing 2.8% of the 2,5-dinitro compound and 0.5% of the trinitro compound.

28 parts of a solid with the following analysis values are obtained from the mother liquor and the sulphuric acid washings: 20.3% of 4,5-dinitro-DHA, 51.9% of 2,5-dinitro-DHA, 3.9% of 2,7-dinitro +2,4,7-trinitro-DHA, 1.0% of 2,4,5-trinitro-DHA and 1.4% of 4-nitro- DHA.

EXAMPLE 4

64 parts of 89.5% pure 1,8-dimethoxy-anthraquinone are dissolved in 740 parts of 96% strength sulphuric acid at 20° C. 92 parts of mixed acid (33% of $HNO_3$, 67% of $H_2SO_4$) are added dropwise to this solution at 0°–5° C. in the course of 3 hours, whilst cooling, and the mixture is subsequently stirred for 1 hour. It is heated to 100°–105° C. in the course of 1 hour, this temperature is maintained for 4 hours, the mixture is then cooled to 20°–25° C. and filtered and the material on the filter is washed with 180 parts of 96% sulphuric acid and then with water. After drying, 64 parts of 98.7% pure 4,5-dinitro-1,8-dihydroxy-anthraquinone, which contains 1% of the 2,5-dinitro derivative, are obtained.

If the mother liquor and the sulphuric acid washings are treated as described in Example 1, 10 parts of by-products are obtained.

Examples 1–4 can also be modified by discharging the entire nitration batch onto ice and treating the entire precipitate with 80–100% strength sulphuric acid so that the by-products dissolve. However, compared with the method described above, this procedure offers no advantages industrially.

We claim:

1. In the preparation and recovery of 4,5-dinitro-1,8-dihydroxy-anthraquinone by reacting 1,8-dihydroxy-anthraquinone or 1,8-dimethoxy-anthraquinone with nitric acid in the presence of sulphuric acid, and thereafter recovering the desired product in solid form from the reaction mass, the improvement which comprises effecting the nitration in the presence of sulphuric acid of a concentration such that, when the nitration reaction and if appropriate the saponification reaction have ended, an 80–100% strength sulphuric acid is present, or such a final sulphuric acid concentration is established by adding water, and effecting the recovery by permitting the reaction mass to stand in the sulphuric acid of 80 to 100% concentration.

2. The process according to claim 1, wherein the starting material is 1,8-dihydroxy-anthraquinone and the final sulphuric acid concentration is from 85 to 90%.

3. The process according to claim 1, wherein the starting material is 1,8-dimethoxy-anthraquinone and the final sulphuric acid concentration is from 90 to 99%.

* * * * *